US010365247B2

(12) United States Patent
Paradise et al.

(10) Patent No.: US 10,365,247 B2
(45) Date of Patent: Jul. 30, 2019

(54) MOVABLE MEMBER ASSEMBLY HAVING A SENSOR ASSEMBLY

(71) Applicant: Hamilton Sundstrand Corporation, Charlotte, NC (US)

(72) Inventors: Bruce D. Paradise, Avon, CT (US); Leo J. Veilleux, Wethersfield, CT (US)

(73) Assignee: HAMILTON SUNDSTRAND CORPORATION, Charlotte, NC (US)

( * ) Notice: Subject to any disclaimer, the term of this patent is extended or adjusted under 35 U.S.C. 154(b) by 327 days.

(21) Appl. No.: 15/262,105

(22) Filed: Sep. 12, 2016

(65) Prior Publication Data

US 2018/0074020 A1    Mar. 15, 2018

(51) Int. Cl.
| G01S 11/14 | (2006.01) |
| G01N 29/07 | (2006.01) |
| G01B 17/00 | (2006.01) |
| G01D 5/48 | (2006.01) |
| G11B 17/00 | (2006.01) |

(52) U.S. Cl.
CPC ............ G01N 29/07 (2013.01); G01B 17/00 (2013.01); G01D 5/48 (2013.01); G01S 11/14 (2013.01); *G01N 2291/011* (2013.01)

(58) Field of Classification Search
CPC .. G01N 29/07; G01N 2291/011; G01B 17/00; G01D 5/48; G01S 11/14
USPC .......................................................... 73/597
See application file for complete search history.

(56) References Cited

U.S. PATENT DOCUMENTS

| H277 H | 5/1987 | Lee et al. |
| 4,769,793 A | 9/1988 | Kniest et al. |
| 6,173,233 B1 | 1/2001 | Janutka et al. |
| 6,435,031 B1 * | 8/2002 | Nagai ..................... G01D 5/00 310/321 |
| 6,585,652 B2 | 7/2003 | Lang et al. |
| 7,360,448 B2 | 4/2008 | Maginnis et al. |
| 9,163,471 B2 | 10/2015 | Coonrod et al. |
| 2005/0223808 A1 * | 10/2005 | Myers .................. G01N 29/024 73/629 |
| 2006/0144217 A1 | 7/2006 | Neumann |

(Continued)

FOREIGN PATENT DOCUMENTS

| CN | 105715620 A | 6/2016 |
| EP | 1806563 A1 | 7/2007 |

(Continued)

OTHER PUBLICATIONS

European Search Report for European Patent Application No. 17190718.1 dated Jan. 18, 2018, 8 pages.

(Continued)

*Primary Examiner* — Justin Seo
*Assistant Examiner* — Rose M Miller
(74) *Attorney, Agent, or Firm* — Cantor Colburn LLP

(57) ABSTRACT

A sensor assembly is provided includes a sensor housing, a first sensor, and a second sensor. The sensor housing operatively connected to a body having a first end and a second end. The first sensor is disposed within the sensor housing. The second sensor is disposed within the sensor housing and is spaced apart from the first sensor. The first sensor and the second sensor face towards a first position feature and a second position feature that is disposed on a movable member that is received within the body.

18 Claims, 4 Drawing Sheets

(56) References Cited

U.S. PATENT DOCUMENTS

| | | | |
|---|---|---|---|
| 2010/0288036 A1* | 11/2010 | Volkwein | G01B 17/00 73/114.29 |
| 2013/0182540 A1 | 7/2013 | Lyons et al. | |
| 2017/0102364 A1* | 4/2017 | Hill | G01N 29/07 |

FOREIGN PATENT DOCUMENTS

| JP | 59062705 A * | 4/1984 | |
|---|---|---|---|
| WO | WO-8501800 A1 * | 4/1985 | ....... B60G 17/01933 |
| WO | 2005003571 A1 | 1/2005 | |
| WO | 2009015741 A1 | 2/2009 | |
| WO | 2015019231 A1 | 2/2015 | |

OTHER PUBLICATIONS

European Office Action for Application No. 17190718.1-1022 dated Oct. 8, 2018, 5 pages.

* cited by examiner

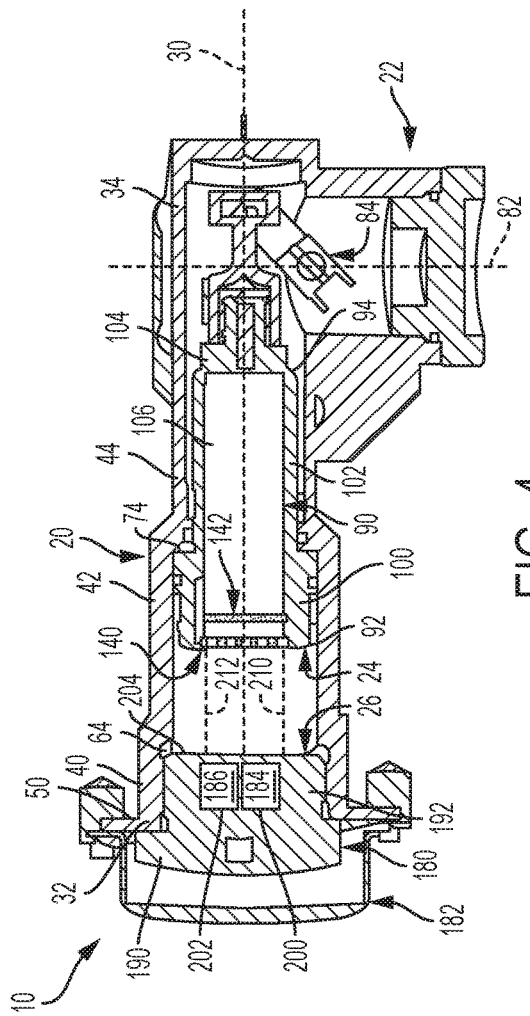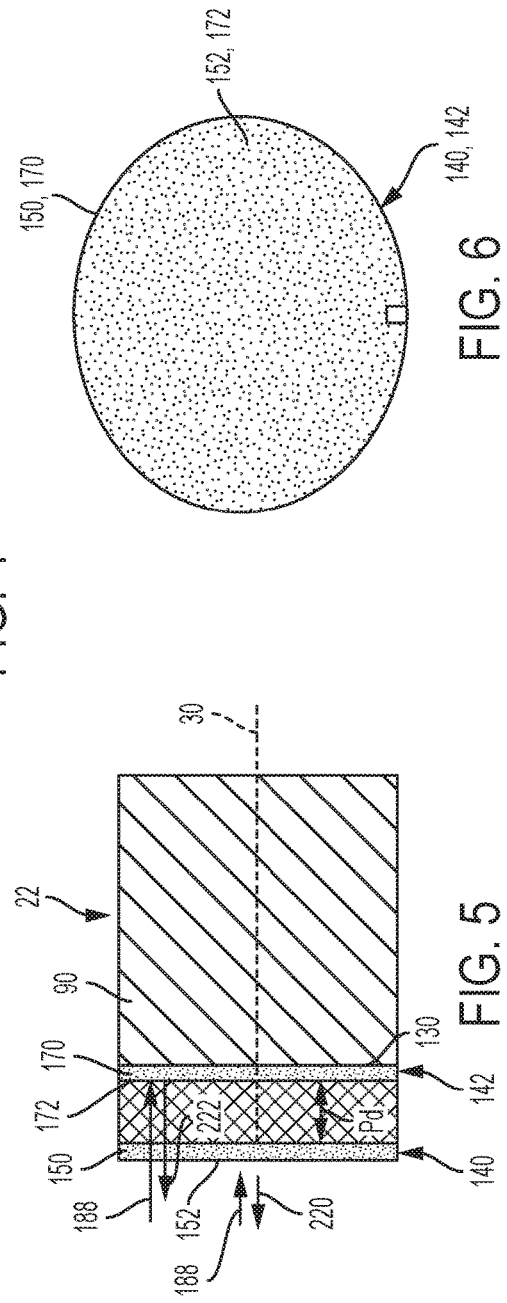

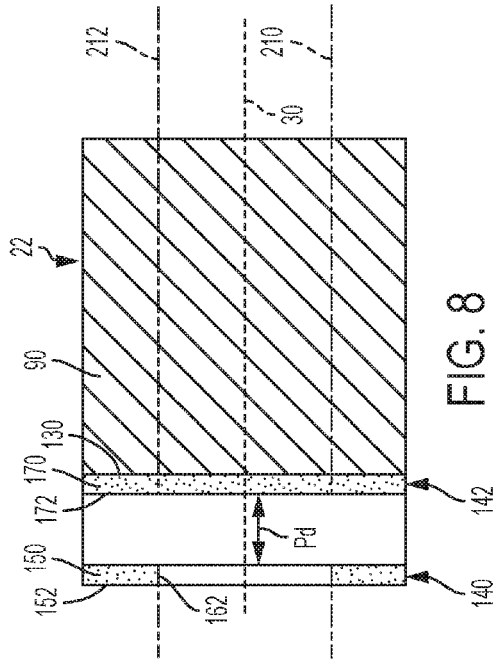
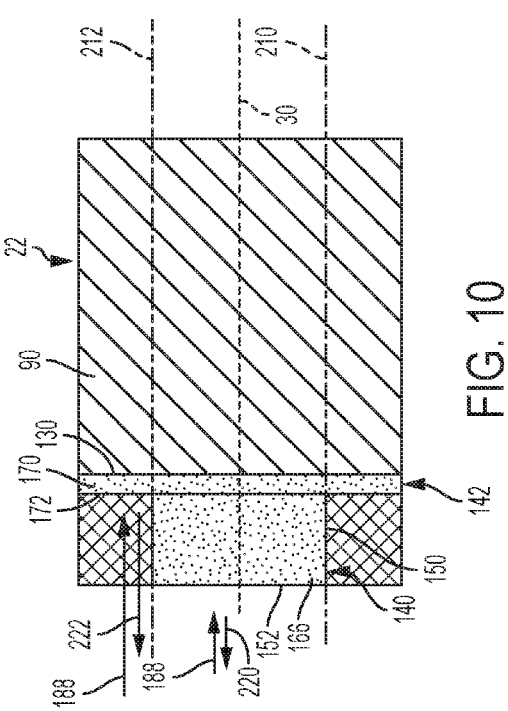
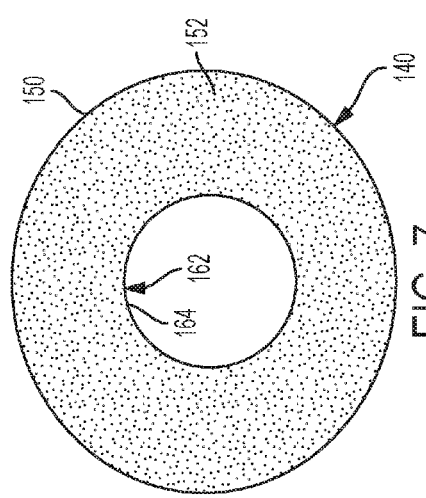
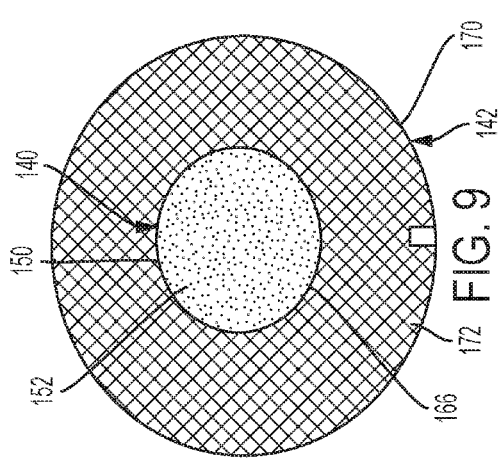

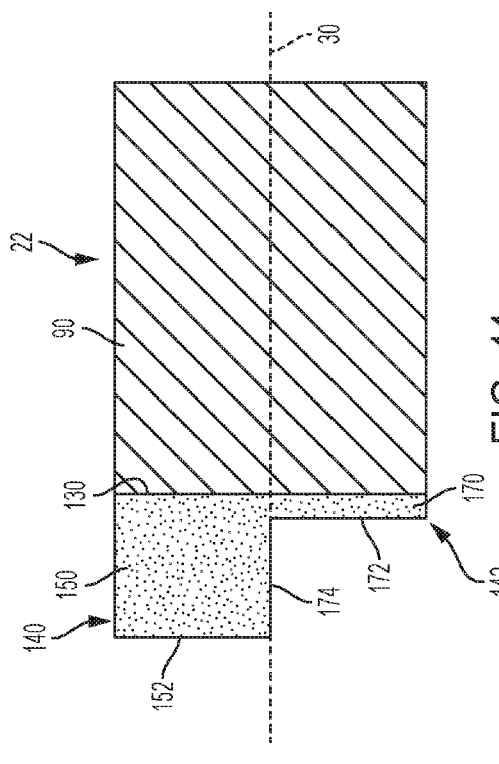
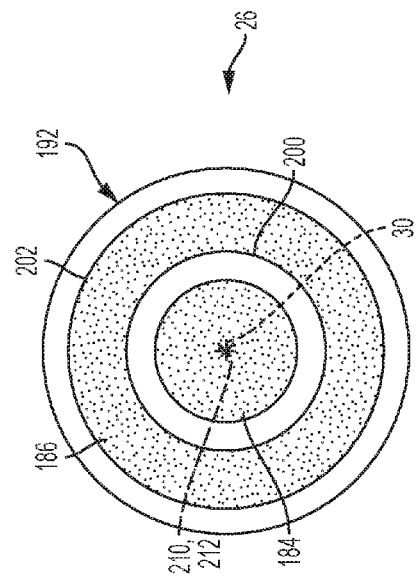
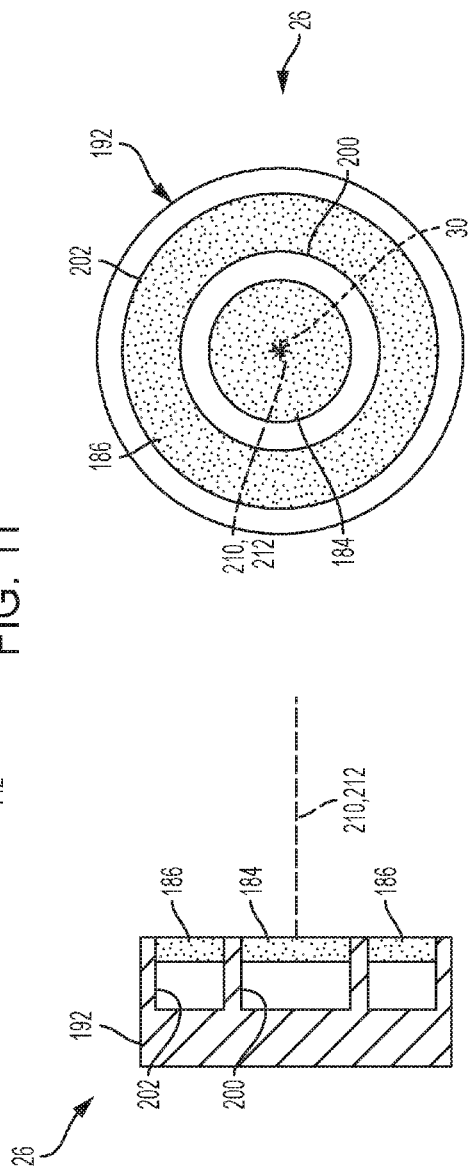

MOVABLE MEMBER ASSEMBLY HAVING A SENSOR ASSEMBLY

BACKGROUND

Sensors are commonly used for measuring the location or position of components provided with valves, pistons, actuators, or the like. The accuracy of the sensor may vary based on the medium in which the sensor is operated, the temperature at which the sensor is operated, or the positioning of the sensor.

BRIEF DESCRIPTION

According to an embodiment of the present disclosure, a movable member assembly is provided. The movable member assembly includes a body, a movable member, and a sensor assembly. The body extends between a first end towards a second end along a body axis. The movable member is slidably disposed within the body. The movable member is provided with a first position feature and a second position feature axially spaced apart from the first position feature. The sensor assembly is disposed proximate the first end. The sensor assembly has a first sensor and a second sensor, configured to detect a position of the movable member by detecting a position of at least one of the first position feature and the second position feature.

According to another embodiment of the present disclosure, a sensor assembly is provided. The sensor assembly includes a sensor housing, a first sensor, and a second sensor. The sensor housing is operatively connected to a body that extends between a first end towards a second end along a body axis. The first sensor is disposed within the sensor housing and is radially spaced apart from the body axis in a first direction. The second sensor is disposed within the sensor housing and is radially spaced apart from the body axis in a second direction. The first sensor and the second sensor face towards a first position feature and a second position feature that is disposed within a cavity of a movable member that is received within the body.

According to yet another embodiment of the present disclosure, a sensor assembly is provided. The sensor assembly includes a sensor housing, a first sensor, and a second sensor. The sensor housing operatively connected to a body having a first end and a second end. The first sensor is disposed within the sensor housing. The second sensor is disposed within the sensor housing and is spaced apart from the first sensor. The first sensor and the second sensor face towards a first position feature that extends from a second position feature that is disposed on a movable member that is received within the body.

BRIEF DESCRIPTION OF THE DRAWINGS

The subject matter which is regarded as the present disclosure is particularly pointed out and distinctly claimed in the claims at the conclusion of the specification. The foregoing and other features, and advantages of the present disclosure are apparent from the following detailed description taken in conjunction with the accompanying drawings in which:

FIG. 4 is a side section view of a second embodiment of a movable member assembly having a sensor assembly;

FIG. 5 is a side section view of a portion of a movable member of the movable member assembly;

FIG. 6 is a perspective view of a reflection surface;

FIG. 7 is a perspective view of a first reflection surface;

FIG. 8 is a side section view of a portion of a movable member of the movable member assembly having the first reflection surface;

FIG. 9 is a perspective view of a first reflection surface and a second reflection surface;

FIG. 10 is a side section view of a portion of a movable member of the movable member assembly having the first reflection surface and the second reflection surface;

FIG. 11 is a side section of a movable of the movable member assembly having a stepped target surface;

FIG. 12 is a partial side view of a dual annular sensor assembly; and

FIG. 13 is a perspective view of the dual annular sensor assembly.

DETAILED DESCRIPTION

Referring now to the Figures, where the invention will be described with reference to specific embodiments, without limiting same, it is to be understood that the disclosed embodiments are merely illustrative and may be embodied in various and alternative forms. The Figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present disclosure.

Vehicles, such as aircraft, are provided with a movable member assembly 10. The movable member assembly is configured to supply metered amounts of a fluid to a system of the aircraft such as a fuel control system, a pneumatic system, a hydraulic system, or the like. A controller or a control system may calculate or determine a desired flow rate that is supplied through the movable member assembly 10 and adjusts a position of a component of the movable member assembly 10 to achieve the desired flow rate.

The temperature of the fluid that is supplied through the movable member assembly 10 may vary and as the temperature of the fluid varies, the density of the fluid varies. The variations in density of the fluid should be accounted for by the controller or control system to ensure accuracy in supplying the desired flow rate to a system of the aircraft.

Figure 1:
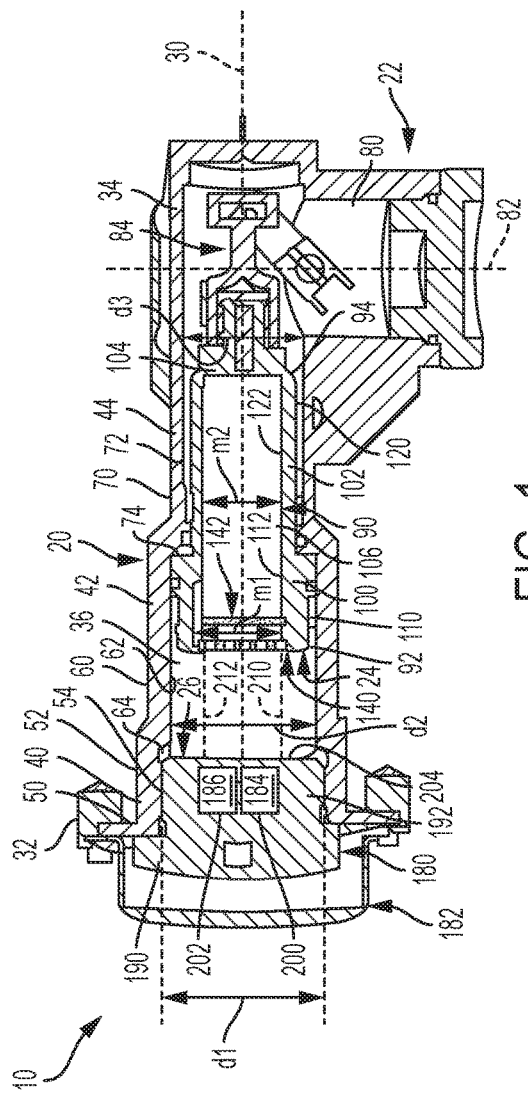
FIG. 1 is a side section view of a first embodiment of a movable member assembly having a sensor assembly.

Referring to FIG. 1, the movable member assembly 10 includes a body 20, a housing 22, a movable member 24, and a sensor assembly 26. The body 20 extends along a body axis 30 between a first end 32 and a second end 34. The body 20 defines a bore 36 that extends from the first end 32 towards the second end 34 along the body axis 30. In at least one embodiment, a diameter of the bore 36 varies along a length of the body 20 from the first end 32 towards the second end 34.

The body 20 includes a first body portion 40, a second body portion 42, a third body portion 44. The first body portion 40 is disposed proximate the first end 32. The first body portion 40 includes a mounting flange 50 that extends radially away from a first body portion outer surface 52 that is disposed opposite a first body portion inner surface 54. The first body portion 40 has a first bore diameter, d1.

The second body portion 42 extends axially from the first body portion 40 along the body axis 30 towards the second end 34. The second body portion 42 includes a second body portion outer surface 60 that is disposed opposite a second body portion inner surface 62. The second body portion 42 has a second bore diameter, d2, which is less than the first bore diameter, d1. A first shelf 64 extends between and is disposed substantially perpendicular to the first body portion inner surface 54 and the second body portion inner surface 62.

The third body portion 44 extends axially from the second body portion 42 along the body axis 30 towards the second end 34. The third body portion 44 includes a third body portion outer surface 70 that is disposed opposite a third body portion inner surface 72. The third body portion 44 has a third bore diameter, d3, which is less than the second bore diameter, d2. A second shelf 74 extends between and is disposed substantially perpendicular to the second body portion inner surface 62 and the third body portion inner surface 72.

The housing 22 is operatively connected to the body 20 proximate the second end 34 of the body 20. The housing 22 defines a housing bore 80 that extends along a housing axis 82 that is disposed substantially transverse to the body axis 30. An actuator 84 is operatively connected to the movable member 24 and is configured to move the movable member 24 between a plurality of positions within the bore 36. The actuator 84 extends between the body 20 and the housing 22. The actuator 84 may be an electro-hydraulic actuator, an electrical actuator, a hydraulic actuator, a pneumatic actuator, or the like that is in communication with the controller or control system.

The movable member 24 is slidably disposed within the bore 36. The movable member 24 includes a movable member body 90 that extends between a first movable member end 92 and a second movable member end 94 along the body axis 30. The movable member body 90 defines a movable member head 100, a movable member extension 102, a movable member connector 104, and a cavity 106.

The movable member head 100 is disposed proximate the first movable member end 92. The movable member head 100 is disposed within the second body portion 42. At least a portion of the movable member head 100 is configured to engage the second shelf 74 based on the position of the movable member 24 within the bore 36. A head outer surface 110 is slidably engaged with the second body portion inner surface 62. A head inner surface 112 is disposed opposite the head outer surface 110. The head inner surface 112 defines a first diameter, m1.

The movable member extension 102 extends between the movable member head 100 and the movable member connector 104. The movable member extension 102 includes an extension outer surface 120 that is disposed opposite an extension inner surface 122. The extension inner surface 122 defines a second diameter, m2, that is less than the first diameter, m1.

The movable member connector 104 extends from the movable member extension 102 towards the second movable member end 94. The movable member connector 104 is operatively connected to the actuator 84.

The cavity 106 extends from the first movable member end 92 towards the second movable member end 94 along the body axis 30. The cavity 106 extends through the movable member head 100 and the movable member extension 102. In at least one embodiment, the cavity 106 extends at least partially through the movable member head 100 and terminates at a movable member surface 130.

Referring to FIGS. 1 and 4, a first position feature 140 and a second position feature 142 are disposed on the movable member 24. The first position feature 140 and the second position feature 142 are disposed within the cavity 106 of the movable member 24. The first position feature 140 and the second position feature 142 are axially spaced apart from each other along the body axis 30. The first position feature 140 and the second position feature 142 are axially spaced apart from each other at a predetermined distance, Pd. The first position feature 140 is disposed closer to the first movable member end 92 than the second position feature 142.

Referring to FIGS. 1-11, the first position feature 140 is configured as a first sheet 150 that defines a first reflection surface 152. The first sheet 150 extends radially between the head outer surface 110, the head inner surface 112, the extension outer surface 120, or the extension inner surface 122. In at least one embodiment, the first sheet 150 is disposed on a generally planar surface that is disposed transverse to the body axis 30 that is disposed proximate the first movable member end 92.

Figure 3:
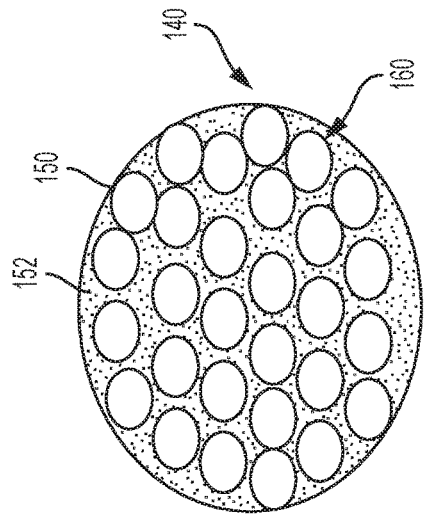
FIG. 3 is a perspective view of a reflection surface.
Figure 2:
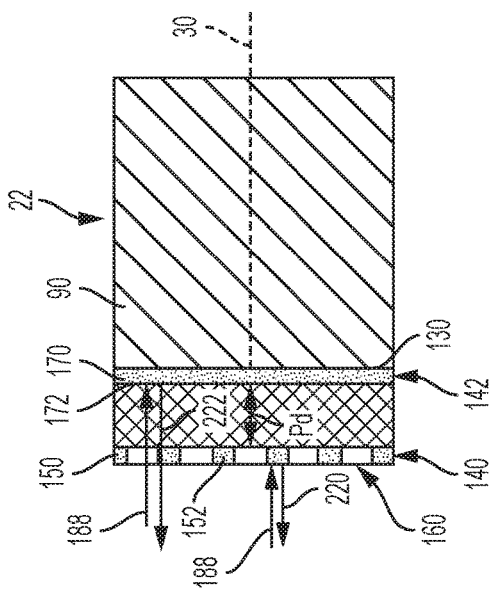
FIG. 2 is a side section view of a portion of a movable member of the movable member assembly.

Referring to FIGS. 1-3, the first sheet 150 is provided with a plurality of openings 160 such that the first sheet 150 is a perforated sheet. The plurality of openings 160 extend through the first reflection surface 152 and interrupt the first reflection surface 152. As such, the first reflection surface 152 is disposed between adjacent openings of the plurality of openings 160.

Referring to FIGS. 4-6, the first sheet 150 is a continuous sheet such that the first reflection surface 152 is uninterrupted. The continuous sheet may be a solid sheet that is free of openings.

Referring to FIGS. 7 and 8, the first sheet 150 is provided with an opening 162. The opening 162 may be a centralized opening that is disposed about the body axis 30. The opening 162 extends through the first reflection surface 152. As such, the first reflection surface 152 extends radially between an edge 164 of the opening 162 towards the head outer surface 110, the head inner surface 112, the extension outer surface 120, or the extension inner surface 122.

Referring to FIGS. 9 and 10, the first sheet 150 is configured as a protrusion 166 that extends from the second sheet 170 of the second position feature 142 along the body axis 30. The protrusion 166 may be configured as a substantially cylindrical protrusion. The protrusion 166 is disposed substantially coaxial with the second position feature 142. The first reflection surface 152 is disposed at a distal end of the protrusion 166 that faces towards the first end 32 of the body 20.

Referring to FIGS. 1-11, the second position feature 142 is configured as a second sheet 170 that defines a second reflection surface 172. The second sheet 170 extends radially between the head outer surface 110, the head inner surface 112, the extension outer surface 120, or the extension inner surface 122. In at least one embodiment, is disposed on the movable member surface 130.

The second sheet 170 is axially spaced apart from the first sheet 150 along the body axis 30. The second sheet 170 is axially spaced apart from the first movable member end 92. The second sheet 170 is a continuous sheet such that the second reflection surface 172 is a solid sheet that is uninterrupted by openings. The second reflection surface 172 is disposed coaxially with the first reflection surface 152 along the body axis 30. In at least one embodiment, the second sheet 170 may have a substantially similar configuration as the first sheet 150 as described above. For example, the second sheet 170 may be provided with a plurality of openings such that it is a perforated sheet, a centralized opening, a protrusion, or the like.

Referring to FIG. 11, the first position feature 140 and the second position feature 142 are configured as a stepped target or multi-surface target for the sensor assembly 26. The first reflection surface 152 of the first sheet 150 of the first position feature 140 is disposed closer to the sensor assembly 26 than the second reflection surface 172 of the second sheet 170 of the second position feature 142. The first reflection surface 152 of the first sheet 150 of the first position feature 140 is disposed substantially parallel to the second reflection surface 172 of the second sheet 170 of the second position feature 142. A step surface 174 extends between the first reflection surface 152 and the second reflection surface. The step surface 174 is disposed substantially parallel to the body axis 30 and is disposed substantially perpendicular to the first reflection surface 152 of the first sheet 150 of the first position feature 140 and the second reflection surface 172 of the second sheet 170 of the second position feature 142. In at least one embodiment, the body axis 30 defines a centerline of the stepped target.

Referring to FIGS. 1 and 4, the sensor assembly 26 is disposed proximate the first end 32 of the body 20. The sensor assembly 26 is spaced apart from the first position feature 140 and the second position feature 142 that are disposed on or within the movable member 24 such that the sensor assembly 26 is in a non-contacting arrangement. The sensor assembly 26 is configured to detect or monitor a position of the movable member 24 within the bore 36 by detecting a position of at least one of the first position feature 140 and the second position feature 142. The position of at least one of the first position feature 140 and the second position feature 142 may be determined, measured, calculated, or based on a signal, wave, or the like that is reflected off of the first reflection surface 152 of the first sheet 150 of the first position feature 140 and a signal, wave or the like that is reflected off of the second reflection surface 172 of the second sheet 170 of the second position feature 142.

The sensor assembly 26 includes a sensor housing 180, a sensor cover 182, a first sensor 184, and a second sensor 186. The sensor housing 180 is disposed proximate the first end 32 of the body 20. The sensor housing 180 is operatively connected to the body 20 proximate the first end 32. The sensor housing 180 includes a first housing portion 190 and a second housing portion 192 that extends from the first housing portion 190. The first housing portion 190 is configured as a flange that engages the mounting flange 50. The first housing portion 190 radially extends towards a radial edge of the mounting flange 50 but is radially spaced apart from the radial edge of the mounting flange 50. The second housing portion 192 extends along the body axis 30 towards the second end 34 of the body 20. The second housing portion 192 is at least partially received within the bore 36 and is at least partially received within the first body portion 40. The second housing portion 192 defines a first receiving pocket 200 and a second receiving pocket 202 that each extend from a face 204 of the second housing portion 192 towards the first housing portion 190.

The sensor cover 182 is disposed over the sensor housing 180. The sensor cover 182 is operatively connected to the mounting flange 50.

The first sensor 184 is disposed within the sensor housing 180. The first sensor 184 is received within the first receiving pocket 200 of the second housing portion 192. The first sensor 184 faces towards the first reflection surface 152 of the first position feature 140 and the second reflection surface 172 of the second position feature 142. The first sensor 184 is radially spaced apart or radially offset from the body axis 30 in a first direction. In at least one embodiment, a first sensor centerline 210 is disposed substantially coaxially with the body axis 30.

The second sensor 186 is disposed within the sensor housing 180. The second sensor 186 is received within the second receiving pocket 202 of the second housing portion 192. The second sensor 186 faces towards the first reflection surface 152 of the first position feature 140 and the second reflection surface 172 of the second position feature 142. The second sensor 186 is radially spaced apart or radially offset from the body axis 30 in a second direction that is disposed opposite the first direction. The first sensor 184 and the second sensor 186 are symmetrically disposed on opposite sides of the body axis 30 such that they are side by side transducers for use with dual channel fadecs. In at least one embodiment, a second sensor centerline 212 is disposed substantially coaxially with the body axis 30.

In at least one embodiment, the first sensor 184 is disposed within the second sensor 186 (as shown in FIGS. 12 and 13) such that the first sensor centerline 210 and the second sensor centerline 212 are each disposed coaxially with the body axis 30 to be a double annular transducer for use with dual channel fadecs. The first sensor 184 is configured as a diameter disc and the second sensor 186 is configured as an annular ring. A surface area of the diameter disc of the first sensor 184 is substantially equal to a surface area of the annular ring of the second sensor 186. A signal output from at least one of the first sensor 184 and the second sensor 186 strikes the stepped target. Approximately 50% of the signal is reflected off of the first reflection surface 152 and approximately 50% of the signal is reflected off of the second reflection surface 172 allowing for the production or formation of a double echo that is received by at least one of the first sensor 184 and the second sensor 186.

The first sensor 184 and the second sensor 186 are configured as an ultrasonic sensor, a Piezo sonic transducer, or the like. The first sensor 184 and the second sensor 186 are configured to transmit, propagate, or otherwise send an ultrasonic wave 188 towards the first reflection surface 152 and the second reflection surface 172. The first sensor 184 and the second sensor 186 are configured to transmit, propagate or otherwise send the ultrasonic wave 188 at the same time, sequentially, periodically, or individually. The first sensor 184 and the second sensor 186 are configured to listen for or receive a reflected ultrasonic wave at the same time, sequentially, periodically, or individually.

The ultrasonic wave 188 provided by at least one of the first sensor 184 and the second sensor 186 reflects off of the first reflection surface 152 to form a first reflection wave 220. The ultrasonic wave 188 propagates through an operating media that is disposed between the first position feature 140 and the second position feature 142 to reflect off of the second reflection surface 172 to form a second reflection wave 222.

At least one of the first sensor 184 and the second sensor 186 is configured to receive the first reflection wave 220 and the second reflection wave 222. A first time-of-flight of the ultrasonic wave 188 is recorded by the controller, control system, or at least one of the first sensor 184 and the second sensor 186 based on a propagation time of the ultrasonic wave 188 towards the first reflection surface 152 and a return time of the first reflection wave 220 towards the first sensor 184 and/or the second sensor 186. A second time-of-flight of the ultrasonic wave 188 is recorded based on a propagation time of the ultrasonic wave 188 towards the second reflection surface 172 and a return time the second reflection wave 222 to towards the first sensor 184 and/or the second sensor 186. The controller or control system is provided with an algorithm or at least one processor programmed to perform a routine or sub-routine that is used to establish a distance from the first sensor 184 and/or the second sensor 186 to at least one of the first reflective surface 152 and the second reflective surface 172 based on at least one of the first time-of-flight, the second time-of-flight, the predetermined distance, Pd, an axial thickness of the first sheet 150, an axial thickness of the second sheet 170, a density of the operating media, and a temperature of the operating media.

Referring to FIG. 2, the first sensor 184 is proximately aligned with the first reflection surface 152 of the first sheet 150 of the first position feature 140 and is proximately aligned with the second reflection surface 172 of the second sheet 170 of the second position feature 142. As such, the first sensor centerline 210 is proximately aligned with a line that intersects at least an edge of the first reflection surface 152 and at least an edge of the second reflection surface 172. In at least one embodiment, the first sensor centerline 210 with an edge of the first reflection surface 152 that is disposed between adjacent openings of the plurality of openings 160. The second sensor 186 is proximately aligned with the second reflection surface 172 and is proximately aligned with the first reflection surface 152 of the first sheet 150 of the first position feature 140. As such, the second sensor centerline 212 is proximately aligned with a line that intersects at least an edge of the first reflection surface 152 and at least an edge of the second reflection surface 172. In at least one embodiment, the second sensor centerline 212 is proximately aligned with an opening of the plurality of openings 160.

Referring to FIG. 5, the first sensor 184 and the second sensor 186 face towards the first reflection surface 152 of the first position feature 140 and the second reflection surface 172 of the second position feature 142.

Referring to FIGS. 7 and 8, the first sensor 184 is proximately aligned with a first edge of the opening 162 and the second sensor 186 is proximately aligned with a second edge of the opening 162 that is radially spaced apart from the first edge of the opening 162. As such, the first sensor centerline 210 is proximately aligned with the first edge of the opening 162 and the second sensor centerline 212 is proximately aligned with the second edge of the opening 162.

Referring to FIGS. 9 and 10, the first sensor 184 is proximately aligned with the first reflection surface 152 that is disposed at the distal end of the protrusion 166. The first sensor centerline 210 is disposed substantially coaxial with the body axis 30. The second sensor 186 is proximately aligned with the second reflection surface 172 that is radially and axially offset from the first reflection surface 152.

Throughout this specification, the term "attach," "attachment," "connected", "coupled," "coupling," "mount," or "mounting" shall be interpreted to mean that a structural component or element is in some manner connected to or contacts another element, either directly or indirectly through at least one intervening structural element, or is integrally formed with the other structural element.

While the present disclosure has been described in detail in connection with only a limited number of embodiments, it should be readily understood that the present disclosure is not limited to such disclosed embodiments. Rather, the present disclosure can be modified to incorporate any number of variations, alterations, substitutions or equivalent arrangements not heretofore described, but which are commensurate with the scope of the present disclosure. Additionally, while various embodiments of the present disclosure have been described, it is to be understood that aspects of the present disclosure may include only some of the described embodiments or combinations of the described embodiments or combinations of the described embodiments. Accordingly, the present disclosure is not to be seen as limited by the foregoing description, but is only limited by the scope of the appended claims.

The invention claimed is:

1. A movable member assembly, comprising:
   a body extending between a first end towards a second end along a body axis;
   a movable member slidably disposed within the body, the movable member provided with a first position feature and a second position feature axially spaced apart from the first position feature; and
   a sonic sensor assembly disposed proximate the first end, the sonic sensor assembly having a first sonic sensor and a second sonic sensor, configured to detect a position of the movable member by detecting a position of at least one of the first position feature and the second position feature, wherein the first position feature is configured as a first sheet that defines a first reflection surface provided with a plurality of openings that interrupt the first reflection surface.

2. The movable member assembly of claim 1, wherein the first reflection surface disposed proximate a first movable member end.

3. The movable member assembly of claim 2, wherein the second position feature is a second reflection surface that is spaced apart from the first movable member end.

4. The movable member assembly of claim 3, wherein the first sonic sensor and the second sonic sensor are disposed within a sensor housing that is operatively connected to the first end of the body.

5. The movable member assembly of claim 4, wherein the first sonic sensor is radially offset from the body axis.

6. The movable member assembly of claim 5, wherein at least one of the first sonic sensor and the second sonic sensor propagates a sonic wave towards the first reflection surface and the second reflection surface.

7. The movable member assembly of claim 6, wherein the sonic wave reflects off of the first reflection surface to form a first reflection wave and the sonic wave reflects off of the second reflection surface to form a second reflection wave.

8. The movable member assembly of claim 7, wherein at least one of the first sonic sensor and the second sonic sensor receives the first reflection wave and the second reflection wave.

9. The movable member assembly of claim 8, wherein the position of the movable member is based on the first reflection wave and the second reflection wave.

10. A sensor assembly, comprising:
    a sensor housing operatively connected to a body that extends between a first end towards a second end along a body axis;
    a first sonic sensor disposed within the sensor housing and radially spaced apart from the body axis in a first direction; and
    a second sonic sensor disposed within the sensor housing and radially spaced apart from the body axis in a second direction, the first sensor and the second sensor face towards a first position feature and a second position feature disposed within a cavity of a movable member that is received within the body, wherein the first position feature is configured as a first sheet that defines a first reflection surface provided with a plurality of openings that interrupt the first reflection surface.

11. The sensor assembly of claim 10, wherein the second position feature is configured as a second sheet that defines a second reflection surface.

12. The sensor assembly of claim 11, wherein the second sonic sensor is proximately aligned with an opening of the plurality of openings.

13. The sensor assembly of claim 10, wherein the first sheet is provided with an opening that is disposed about the body axis.

14. The sensor assembly of claim 13, wherein the first sonic sensor is proximately aligned with a first edge of the opening and the second sonic sensor is proximately aligned with a second edge.

15. A sensor assembly, comprising:
- a sensor housing operatively connected to a body having a first end and a second end;
- a first sonic sensor disposed within the sensor housing; and
- a second sonic sensor disposed within the sensor housing and spaced apart from the first sensor, the first sensor and the second sensor face towards a first position feature that extends from a second position feature disposed on a movable member that is received within the body, wherein the first position feature is configured as a first sheet that defines a first reflection surface provided with a plurality of openings that interrupt the first reflection surface.

16. The sensor assembly of claim 15, wherein the first position feature is configured as a protrusion that defines a first reflection surface.

17. The sensor assembly of claim 16, wherein the second position feature is configured as a second sheet that defines a second reflection surface.

18. The sensor assembly of claim 17, wherein the first reflection surface is disposed concentrically with the second reflection surface.

* * * * *